United States Patent
Zakim et al.

[11] Patent Number: 5,848,977
[45] Date of Patent: Dec. 15, 1998

[54] SAMPLE HOLDER FOR CELLS

[75] Inventors: David S. Zakim, Armonk; Max Diem, Croton-On-Hutson, both of N.Y.

[73] Assignee: InPhoCyte, Inc.

[21] Appl. No.: 602,971

[22] Filed: Feb. 16, 1996

[51] Int. Cl.⁶ .................................................. A61B 5/00
[52] U.S. Cl. ................................... 600/562; 422/101
[58] Field of Search ........................... 600/562, 565, 600/571; 422/101

[56] References Cited

U.S. PATENT DOCUMENTS

| | | | |
|---|---|---|---|
| 1,311,017 | 7/1919 | Skoglund | 422/101 |
| 3,224,434 | 12/1965 | Molonut et al. | 600/562 |
| 3,298,411 | 1/1967 | Rosett | 600/562 |
| 3,379,093 | 4/1968 | Ard . | |
| 3,515,490 | 6/1970 | Dreyfus et al. | 356/244 |
| 3,521,963 | 7/1970 | Bader | 356/244 |
| 4,017,192 | 4/1977 | Rosenthal | 356/201 |
| 4,515,165 | 5/1985 | Carroll | 128/664 |
| 4,661,913 | 4/1987 | Wu et al. | 364/500 |
| 4,729,949 | 3/1988 | Weinreb et al. | 435/30 |
| 4,778,593 | 10/1988 | Yamashita et al. | 209/3.1 |
| 4,787,988 | 11/1988 | Bertoncini et al. | 422/101 |
| 4,832,483 | 5/1989 | Verma | 356/39 |
| 4,849,061 | 7/1989 | Relyea | 422/101 |
| 5,038,039 | 8/1991 | Wong et al. | 250/339 |
| 5,108,381 | 4/1992 | Koloski | 600/562 |
| 5,139,685 | 8/1992 | de Castro et al. | 422/101 |
| 5,168,162 | 12/1992 | Wong et al. | 250/339 |
| 5,171,995 | 12/1992 | Gast et al. | 250/339 |
| 5,174,162 | 12/1992 | Miyake et al. | 73/864.21 |
| 5,240,861 | 8/1993 | Bieri | 436/178 |
| 5,261,410 | 11/1993 | Alfano et al. | 128/664 |
| 5,266,209 | 11/1993 | Knight et al. | 210/691 |
| 5,270,212 | 12/1993 | Horiuchi et al. | 436/45 |
| 5,308,483 | 5/1994 | Sklar et al. | 210/232 |
| 5,408,306 | 4/1995 | Anderson | 356/36 |
| 5,466,572 | 11/1995 | Sasaki et al. | 435/2 |
| 5,470,757 | 11/1995 | Gagnon et al. | 422/58 |
| 5,484,572 | 1/1996 | Katakura et al. | 422/101 |
| 5,528,368 | 6/1996 | Lewis et al. | 356/346 |

FOREIGN PATENT DOCUMENTS

| | | |
|---|---|---|
| 932551 | 8/1973 | Canada . |
| 991438 | 6/1976 | Canada . |
| 1036385 | 8/1978 | Canada . |
| 1057078 | 6/1979 | Canada . |
| 1138218 | 12/1982 | Canada . |
| 1222566 | 6/1987 | Canada . |
| 1242593 | 10/1988 | Canada . |
| 1261256 | 9/1989 | Canada . |
| 1269929 | 6/1990 | Canada . |
| 2019865 | 6/1990 | Canada . |
| 2012291 | 11/1990 | Canada . |
| 2005622 | 6/1991 | Canada . |
| 2007267 | 7/1991 | Canada . |
| 2036031 | 1/1992 | Canada . |
| 2103446 | 12/1992 | Canada . |
| 2136423 | 9/1994 | Canada . |
| 2106507 | 3/1998 | Canada . |
| 90/15981 | 12/1990 | WIPO . |
| 93/00580 | 1/1993 | WIPO . |

OTHER PUBLICATIONS

Blout, E.R. and Mellors, R.C.; "Infrared Spectra Of Tissues"; (1949); Science 110, pp. 137–138.

Schwarz, H.P., Riggs, H.E., Cameron, W., Beyer, E., Jaffe, B., and Trombetta, L.: "Infrared Spectroscopy Of Tissues. Effect Of Insulin Shock" (1951); Proc. Soc. Exptl. Biol. Med. 76, pp. 267–275.

Wood, DL. "Infrared Microspectrum Of Living Muscle Cells"; (1951); Science 114, pp. 36–38.

(List continued on next page.)

*Primary Examiner*—Max Hindenburg
*Attorney, Agent, or Firm*—Hale and Dorr LLP

[57] ABSTRACT

A biological cell sample holder for use in vibrational spectroscopy. The sample holder includes a rectangular body that has a central relief area and an opening through the relief area. A porous membrane is disposed in the opening and a metal coated disk is disposed on top of the porous membrane. The disk has pores of a predetermined size to allow fluid to pass through the disk but retain cells of interest on the disk.

8 Claims, 4 Drawing Sheets

OTHER PUBLICATIONS

Wood, D.L. and Sutherland, G.B.B.M.; "Infrared Spectra Of Muscle Cells"; (1952); Fed. Proc. 11, p. 175.

Morales, M.F. and Cecchini, L.P. "Some Studies On The Infrared Absorption Of The Contractile System Of Skeletal Muscle"; (1951); J. Cell Comp. Physiol. 37, pp. 107–135.

Schwarz, H.P., Riggs, H.E., Glick, C., McGrath, J., Cameron, W., Beyer, B., Bew, E., Jr., and Childs, R.; "Infrared Spectroscopy Of Brain Tissue. A Lipid Fraction In Normal And Irradiated Adult And Fetal Rats"; (1952); Proc. Soc. Exptl. Biol. Med. 80, pp. 467–473.

Schwarz, H.P., Riggs, H.E., Glick, C., McGrath, J., Childs, R., Bew, E., Jr., and Stone, F. "Infrared Spectroscopy Of Liver Glycogen In Normal And Irradiated Adult And Fetal Rats"; (1954); Proc. Soc. Exptl Biol. Med. 85, pp. 96–101.

Manfait, M. and Theophanides, T.; "Fourier Transform Infrared Spectra Of Cells Trated With The Drug Adriamycin"; (1983); Biochem. Biophys. Res. Communs. 116, pp. 321–326.

Beneddetti, E., Papineschi, F., Vergamini, P., Consolini, R., and Spremolla, G.; "New Possibilities Of Research In Chronic Lymphatic Leukemia Cells (CLL)–I"; (1984); Leukemia Research 8, pp. 483–489.

Benedetti, E., Palatresi, M.P., Vergamini, P., Papineschi, F., and Spremolla, G.; "New Possibilities Of Research In Chronic Lymphatic Leukemia By Means Of Fourier Transform–Infrared Spectroscopy–II"; (1985); Leukemia Research, 9, pp. 1001–1008.

Benedetti, E., Vergamini, P., Spremolla, G.; "FT–IR Analysis Of A Single Human Leukemic Cell (abstract)"; Paper presented at the 6th International Conference of Fourier Transform Spectroscopy, Vienna; (1987); Mikrochimica Acta 1988, pp. 139–141.

Wong, P.T.T., Zahab, D.M., Narang, S.A., and Sung, W.L.; "High Pressure Infrared Spectroscopic Study Of Human Proinsulin Gene Expression In Live *Escherichia Coli* Cells"; (1987); Biochem. Biophys. Res. Communs., 146, pp. 232–239.

Benedetti, E., Teodori, L., Vergamini, P. et al; "Fourier Transform Infrared Spectroscopy (FT–IR) with Flow Cytometric Analysis In Tumor Cell Characterization (abstract)"; (1987); Basic Appl. Histochem. 31 (Suppl. 2) p. 14.

Auger, M., Jarrell, H.C., Smith, I.C.P. Wong, P.T.T., Siminovitch, D.J., and Mantsch, H.M.; "Pressure–Induced Exclusion of a Local Anesthetic from Model and Nerve Membranes"; (1987); Biochemistry 26, pp. 8513–8516.

Spremolla, G., Benedetti, E., Vergamini, P., Andreucci, M.C., Macchia, P.; "An Investigation of Acute Lymphoblastic Leukemia (ALL) in Children by Means of Infrared Spectroscopy. Part IV"; (1988); Haematologica 73, pp. 21–24.

Takahashi, H., French, S.W., and Wong, P.T.T.; "High Pressure Fourier Transform Infrared Spectroscopic Study on Molecular Structure of Lipids and Proteins in the Liver of Rats Chronically Fed Ethanol"; (1989); Hepatology 10, p. 705.

Rigas, B, Morgello, S., Goldman, I.S., and Wong, P.T.T.; "Human colorectal cancers display abnormal Fourier–transform infrared spectra"; (1990); Proc. Nat'l Acad. Sci. U.S.A. 87, pp. 8140–8144.

Wong, P.T.T. and Rigas, B.; "Infrared Spectra of Microtome Sections of Human Colon Tissues"; (1990); Appl. Spectros. 44, pp. 1715–1718.

Benedetti, E., Teodori, L., Trinca, M.L., Vergamini, Pl, Salvati, F., Mauro, F., and Spremolla, G.; "A New Approach to the Study of Human Solid Tumor Cells by Means of FT–IR Microspectroscopy"; (1990); Appl. Spectros. 44, pp. 1276–1280.

Choo, L–P., Jackson, M., Halliday, W.C., and Mantsch, H.M.; "Infrared spectroscopic characterisation of multiple sclerosis plaques in the human central nervous system"; (1993); Biochim. Biophys. Acta 1182, pp. 335–337.

Schmidt–Ullrich, R., Verma, S.P., and Wallach, D.F.H.; "Concanavalin A Stimulation Modifies the Lipid and Protein Structure of Rabbit Thymocyte Plasma Membranes. A Laser Raman Study"; (1976); Biochim. Biophys. Acta 426, pp. 477–488.

Verma, S.P., and Wallach, D.F.H.; "Erythrocyte membranes undergo cooperative, pH–sensitive state transitions in the physiological temperature range: Evidence from Raman spectroscopy"; (1976); Proc. Nat'l Acad. Sci., USA 73, pp. 3558–3561.

Frank, C.J., McCreery, R.L., Redd, D.C.B., and Gansler, T.S.; "Detection of Silicone in Lymph Node Biopsy Specimens by Near–Infrared Raman Spectroscopy"; (1993); Appl. Spectroscopy 47, pp. 387–390.

East, E.J., Chang, R.C.C., Yu, N–T, and Kuck, J.F.R.; "Raman Spectroscopic Measurement of Total Sulfhydryl in Intact Lens As Affected by Aging and Ultraviolet Irradiation"; (1978); J. Biol. Chem. 253, pp. 1436–1441.

Wong, P.T.T., Goldstein, S.M., Grekin, R.C., Godwin, T.A., Pivik, C., and Rigas, B.; "Distinct Infrared Spectroscopic Patterns of Human Basal Cell Carcinoma of the Skin"; (1993); Cancer Res. 53, pp. 762–765.

Wong, P.T.T., Wong, R.K., Caputo, T.A., Godwin, T.A., and Rigas, B.; "Infrared spectroscopy of exfoliated human cervical cells: Evidence of extensive structural changes during carcinogenesis"; (1991); Proc. Natl. Acad. Sci. USA 88, pp. 10988–10992.

Yu, N–T, DeNagel, D.C., Ho, D.J–Y, and Kuck, J.F.R.; "Ocular Lenses" in Spiro, T.G., ed. (1987); Biological Applications of Raman Spectroscopy, vol. 1, John Wiley & Sons, N.Y., N.Y., pp. 47–81.

Sokolov, K.V., Byramova, N.E., Mochalova, L.V., Tuzikov, A.B., Shiyan, S.D., Bovin, N.V., and Nabiev, I.R.; "Dectection of Sialic Acid Residues and Studies of Their Organization in Normal and Tumor $a_1$–Acid Glycoproteins as Probed by Surface Enhanced Raman Spectroscopy"; (1993); Appl. Spectroscopy 47, pp. 535–538.

Baraga, J.J., Feld, M.S., and Rava, R.P.; "Rapid Near–Infrared Raman Spectroscopy of Human Tissue with a Spectrograph and CCD Detector"; (1992); Appl. Spectros. 46, pp. 187–190.

Abraham, J.L. and Etz, E.S.; "Molecular Microanalysis of Pathological Specimens in situ with a Laser–Raman Microprobe"; (1979); Science 206, pp. 716–717.

Parker, F.S. and Ans, R.; "Infrared Studies of Human and Other Tissues by the Attenuated Total Reflection Technique"; (1967); Anal. Biochem. 18, pp. 414–422.

Riddle, J.W., Kabler, P.W., Kenner, B.A., Bordner, R.H., Rockwood, S.W., and Stevenson, H.J.R.; "Bacterial Identification by Infrared Spectrometry"; (1956) J. Bacteriol. 72, pp. 593–603.

May, L. and Grenell, R.G., "Infrared Spectral Studies of Tissues", (1957); Ann. N.Y. Acad. Sci. 69, pp. 171–189.

Jeannesson, P., Mainfait, M., Jardillier, J–C, A Technique for Laser Raman Spectroscopic Studies of Isolated Cell Populations; (1983); Anal. Biochem. 129, pp. 305–309.

Ozaki, Y., Mizuno, A., and Kaneuchi, F.; "Structural Differences between Type I and Type IV Collagen in Biological Tissues Studied in Vivo by Attenuated Total Reflection/Fourier Transform Infrared Spectroscopy"; (1992); Appl. Spectroscopy 46, pp. 626–630.

Helm, D., Labischinski, H., Schallen, G., and Naumann, D.; "Classification and identification of bacteria by Fourier–transform infrared spectroscopy"; (1991); J. General Microbiology 137, pp. 69–79.

Woernley, D.L.; "Infrared Absorption Curves for Normal and Neoplastic Tissues and Related Biological Substances"; (1952); Cancer Res. 12, pp. 516–523.

Ghiamati, E., Manoharan, R., Nelson, W.H., and Sperry, J.F.; "UV Resonance Raman Spectra of Bacillus Spores"; (1992); Appl. Spectroscopy 46, pp. 357–364.

Wallon, J., Tong. J., Yan, S.H., and Meurens, M., "Identification of Breast Carcinomatous Tissue by Near Infrared Reflectance Spectroscopy"; (1994); Appl Spectroscopy 48, pp. 190–193.

Naumann, D., Fijala, V., Labischinski, H., and Giesbrecht, P.; "The Rapid Differentiation and Identification of Pathogenic Bacteria Using Fourier Transform Infrared Spectroscopic and Multivariate Statistical Analysis"; (1988); J. Molec. Struct. 174, pp. 165–170.

Polavarapu, P., Chen, G.C. and Deng, Z.; "Polarization–Division Interferometry: Approach for Biomedical Infrared Imaging"; (1994); Soc. Appl. Spect. vol. 48, pp. 1403–1409.

Pezolet, M., et al., "Laser Raman Spectroscopy of Intact Single Muscle Fiber Protein Conformations"; (1973); Biochim. Biophys. Acta 533, pp. 263–269.

Dong, A., Messerschmidt, R.G., Reffner, J.A., and Caughey, W.S.; "Infrared Spectroscopy of a Single Cell– the Human Erythrocyte." (1988) Biochem. and Biophys. Research Communications, 156, pp. 752–756.

Polavarapu, P. and Chen, G–C.; "Polarization–Division Interferometry: Far–Infrared Dichroism"; (1994); Appl. Spect. vol. 48, pp. 1410–1418.

Aldrich Chemical Company, Inc. Catalog, 1988, pp. 1947–1949.

Fischer Scientific Catalog, 1988, pp. 418–421.

SAMPLE HOLDER FOR CELLS

FIELD OF THE INVENTION

The present invention relates to sample holders that are used for the collection, concentration, and preparation of various types of cells that may be analyzed by vibrational spectroscopy.

BACKGROUND TO THE INVENTION

Examination of cells and tissues, referred to as diagnostic pathology, remains critical for reaching a medical diagnosis and selecting the most appropriate therapy for patients. The practice of pathology is needed in reaching definitive diagnoses, but in many instances pathology falls short of clinical needs because of the difficulty in identifying morphological changes in individual cells that definitively indicate the presence of disease. This is an especially significant problem when cells and not intact blocks of tissue are available for examination.

Statistics show that the incidence of cancer is rising while at the same time the incidence of other diseases, e.g., heart disease, is decreasing and people are living longer. We have learned, however, that most cancers, especially those of an epithelial origin, have precancerous antecedents. If these antecedents are detected early and treated, the evolution of precancer to cancer may be avoided. This may be accomplished by finding the disease in its precancerous stages in cells and thereby preventing the emergence of frank cancer from these precancerous cells by removing the affected cells.

The current best method for detecting precancer is microscopic examination of cells usually from epithelial structures. The accuracy and clinical value of microscopic examination of cells, which may form a basis for making definitive pathological and clinical diagnoses, is becoming increasingly important and may provide a method of detecting stages of precancer and cancer without the need for tissue.

Cells from many epithelial structures are easily accessible and can be removed safely, rapidly, and with limited cost and inconvenience to the person being examined. Cells from epithelical structures are useful for screening apparently healthy populations for evidence of the early stages of diseases such as cancer. For example, cervical cells may be examined to detect precancer and/or early stages of cancer of the cervix; cells in urine may be examined for evidence of early stages of urogenital cancers; and cells in sputum may be examined for early diagnosis of lung cancer. These kinds of "cytological" tests are becoming increasingly important in the practice of medicine and for public health.

Microscopic examination of cells has a number of problems. The biggest are high rates of false negative and false positive results. Both of these results impact negatively on patient confidence and add unnecessarily to the costs of health care. Even if the microscopic examination method was completely satisfactory, another problem that arises is that there is an insufficient number of cytotechnologists in the United States. This prevents the expansion of the concept of cytological screening to healthy people for evidence of precancer and early stages of cancer from reaching its full potential. The problem is more acute outside the United States in the developing world where there are severe shortages of personnel trained in cytology and pathology. As such, effective and accurate screening programs are not available for any of the epithelial cancers. Therefore, the control of cancer will depend on more advanced methods for detecting cells in a precancerous stage and for grading the extent to which pre cancerous disease approaches frank cancer.

It is highly desirable to have methods that do not require highly trained personnel for the collection of cells or the data which identify certain cells as affected by precancer or early stages of cancer. What also is desirable is to have a cytological system that extracts the relevant data from cells by automated, machine-based technologies and then interprets this data on-line.

It is known that vibrational spectra from whole cells are sensitive for measuring whether the molecules in cells are normal or abnormal. The abnormalities in the vibrational spectra of cells correlate with the results obtained by microscopic examination of the tissue and cells. Copending application Ser. No. 08/523,972, titled "A System and Method for Diagnosis of Disease By Infrared Analysis of Human Tissues and Cells" filed Jun. 7, 1995, demonstrates that vibrational spectroscopy of epithelial cells can be used to detect stages of precancer. The method of the copending application also detects the evolution of normal cells through a continuum of precancerous changes that eventuate in cancer through spectroscopic examination of such cells. The infrared method further detects the evolution of cells through stages of dysplasia in a number of different pathways in the accumulation of genotype and phenotype abnormalities. According to this method, the acquisition of the spectroscopic data-base can be coupled on-line with appropriate software algorithms for making medically relevant diagnoses on the basis of various spectra collected.

At the present time, there is no reliable, rapid, technologically simple, and inexpensive method for preparing cells for examination by vibrational spectroscopy. This limits the application of spectroscopic technology to medical diagnostics for many reasons, such as the high costs of materials and labor needed to prepare suitable samples for spectral examination.

Standard methods for preparing cells for pathological examination, include fixing, embedding, and staining such cells prior to microscopic examination but are not suitable for preparing cells for spectroscopic examination. This is so because these prior methods for preparing calls for microscopic examination utilize sample holders that are not transparent to infrared light.

The methods used by spectroscopists to study inanimate matter are not useful for point-of-care analysis using vibrational spectroscopy because they are time-consuming, labor intensive, and use expensive infrared transparent windows as sample holders. These methods used by spectroscopists also require a high degree of skill on the part of the operator, which further prevents the general application of vibrational spectroscopy for the diagnosis of disease.

Copending application Ser. No. 08/523,972, titled "A System and Method for Diagnosis of Disease By Infrared Analysis of Human Tissues and Cells," mentioned previously, also describes a system that is capable of rapidly preparing cells for examination by vibrational spectroscopy. Also, copending application Ser. No. 08/485,366, titled "Biological Cell Sample Holding for Use In Infrared and/or Raman Spectroscopy Analysis," filed Jun. 7, 1995, describes a sample holder that may be used in preparing cells for examination. This sample holder will permit the filtration of suspensions of cells onto thin, porous, infrared-transparent material. This sample holder is easy to use, allows the cells to be prepared quickly, and makes cell preparation relatively inexpensive.

It is desirable, however, to have a sample holder that will allow for the direct transfer of cells from collection devices, such as brushes or spatulas, to the sample holder for measurement of the vibrational spectra of the transferred cells. It also is desirable to have a sample holder that will permit the adding of cells to it for examination by vibrational spectroscopy, and the sample holder may be made from porous or nonporous material that is not transparent to infrared energy. It is further desirable to have a sample holder to which cells can be added, and that this sample holder can be used for measuring sequentially the vibrational spectra of the cells and for microscopic examination of stained cells.

SUMMARY OF THE INVENTION

The present invention is a sample holder for use in vibrational spectroscopy. The sample holder of the present invention includes a body with a relief area in the center. An opening is disposed through the relief area. A porous membrane is fixed in the opening. When the porous membrane is fixed in the opening, there is open area below it and a small recess above it. A porous disk with a predetermined pore size is disposed in the recess above the porous membrane.

The sample holder of the present invention allows the addition of a suspension of cells and other components in a fluid medium to the disk which selectively retains cells. According to the sample holder of the present invention, cells are trapped on the surface of the disk while all other components are filtered through the disk and porous membrane. This obviates the need to concentrate cells by some method independent of placing them on the disk. At the same time, trapping the cells on a disk makes it possible to wash the cells extensively, treat them chemically in many different ways, and then to wash away any contaminants that might alter the vibrational spectra. This includes the ability to remove any contaminants that might be added to the collecting medium to facilitate preparation of the cells.

The present invention requires no change in the manner in which cells are collected. For example, epithelial cells may be collected using brushes and spatulas. Moreover, cells can be collected using fine needle aspiration of solid tissues, or, with respect to other areas, in conventional ways from the sputum, urine, cerebrospinal fluid, ascitic fluid, pleural fluid, or any other body fluid.

The present invention provides for adding collected cells to suitable sample holders that hold the cells for reflectance spectroscopy for the purpose of obtaining a vibrational spectra. The vibrational spectra can be in any range of the infrared region and can be obtained by infrared, Raman or resonance Raman spectroscopy.

An object of the present invention is to provide a sample holder that is capable of receiving to all types of cells from any type of body fluid, solid tissue, tissue culture, or organism.

Another object of the present invention is to provide a sample holder to which it is easy to add cells and it is inexpensive.

It is a further object of the present invention to provide a disposable sample holder.

An object of the present invention is to provide a method for chemically fixing cells as they are collected and rapidly removing of fixative from the cells.

A still further object of the present invention is to provide a method for rapidly collecting cells, preparing the cells for analysis by vibrational spectroscopy, and collecting the relevant spectral information at the point of care.

DESCRIPTION OF THE INVENTION

Figure 1:
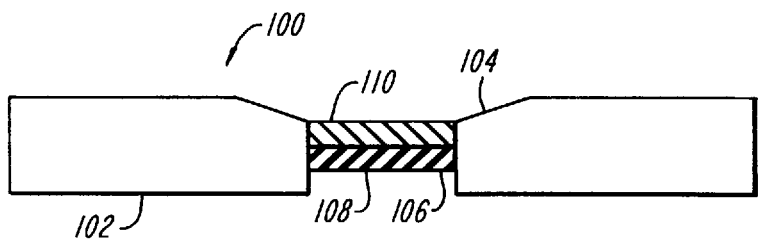
FIG. 1 is a cross-sectional view of a first embodiment of the sample holder of the present invention.

The present invention is a sample holder for use in vibrational spectroscopy. The sample holder of the present invention may be used for collecting and concentrating any types of cells that are capable of being introduced to the sample holder. The collection method for cells can be conventional, such as using brushes, spatulas, or fine needle aspiration. This also includes collecting cells in a fluid medium.

The present invention provides a rapid and inexpensive method for concentrating cells collected with collection devices. The processed cells are then subjected to infrared irradiation and infrared spectra are obtained for any desired region of interest, using reflectance spectroscopy. Alternatively, Raman or resonance Raman spectra may be collected (backscattering) using appropriate frequencies for excitation. The present invention also allows for the efficient direct transfer of cells from collecting devices to the disk of the sample holder. The present invention also provides a method by which cells can be deposited on suitable sample holders by scraping collecting devices across the surface of the sample holder. Moreover, the present invention permits cells on a single sample holder to be prepared simultaneously for examination by infrared spectroscopy and for examination by standard microscopic methods.

Generally, the sample holder of the present invention includes a rectangular body that has a circular relief area. There is an opening that extends through body at the relief area. A porous membrane is fixed in the opening. When the porous membrane is positioned in the opening, there is an open area below the porous membrane and a small recess above it. A porous disk is disposed in the recess. The opening may be circular, square, rectangular, or other shape, and the porous membrane and disk will have corresponding shapes. The disk/porous membrane may be transparent to light of the frequencies of interest. The disk/porous membrane of the sample holder of the present invention have predetermined optical requirements.

The disk/porous membrane may be made from material that is transparent or opaque to infrared light in any frequency range. As such, they both may be made from nylon, Teflon, glass fiber, polyesters, cellulose acetate, and any other suitable material.

In the preferred embodiment of the invention, the top surface of the disk/porous membrane is coated with a thin layer of metal. This metal may be copper, silver, gold, or other highly reflective metal. The metal coating is applied in such a manner that the pores of the disk are not occluded. The metal is intended not to be infrared absorbing. The metal coating facilitates conducting reflectance spectroscopy. Reflection spectroscopy also may be carried out with uncoated disks but is less efficient. Further, the reflected spectra for infrared opaque, uncoated disks can contain spectral bands that are not desired. Having now discussed the sample holder of the present invention in general, the specific embodiments will now be discussed referring to the drawings.

Figure 2:
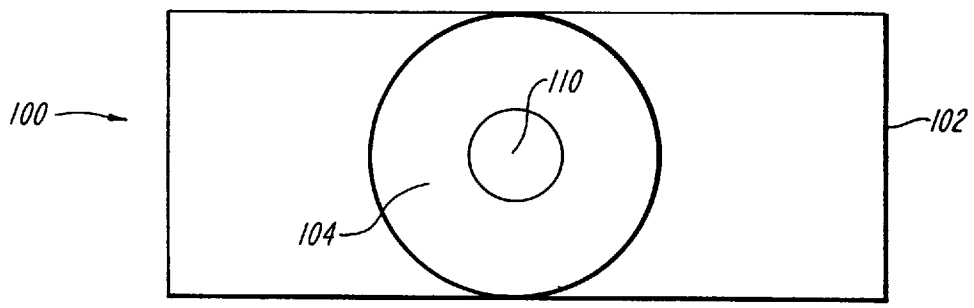
FIG. 2 is a top view of the first embodiment of the sample holder of the present invention.
Figure 3:
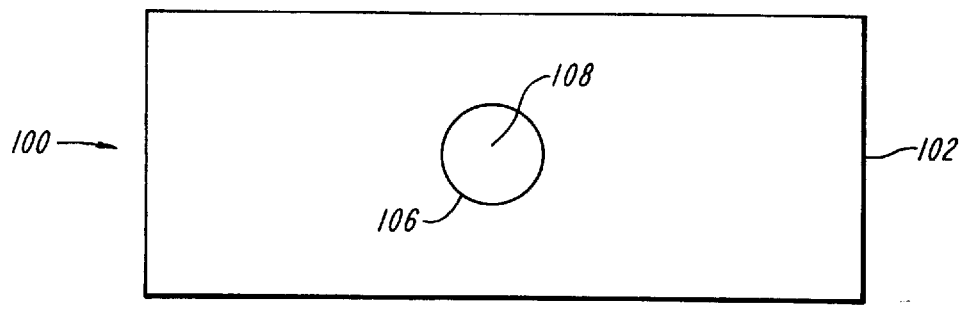
FIG. 3 is a bottom view of the first embodiment of the sample holder of the present invention.

Referring to FIGS. 1, 2, and 3, the sample holder of the present invention is shown generally at 100. The sample holder includes rectangular body 102 having circular relief area 104. At the center of relief area 104 is circular opening 106. Porous membrane 108 is fixed in opening 106. When this is done, a small recess is formed above; porous membrane 108 has a pore size sufficient for passing fluid and non-cell material therethrough.

Figure 6:
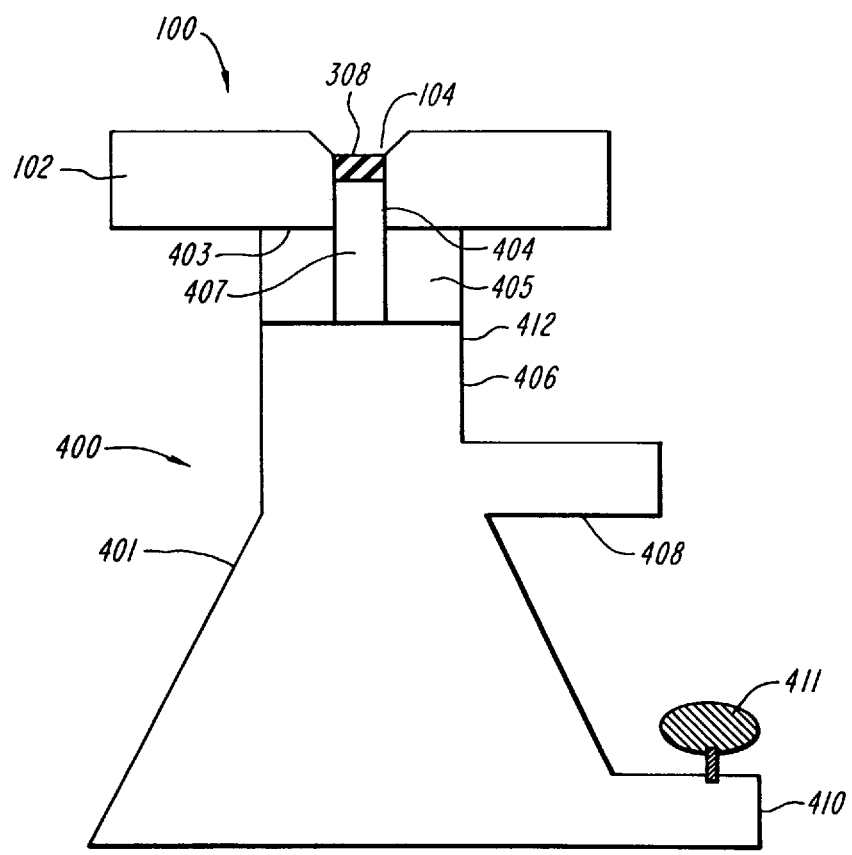
FIG. 6 shows a sample holder of the present invention disposed in a vacuum flask with frit.

Metal coated disk 110 fits into the recess area above porous membrane 108. By disk 110 being positioned in the recess area, the disk will not slide around and will remain in its proper place. The opening below porous membrane 108 is dimensioned to fit to a mounting frit of a vacuum flask (FIG. 6).

Again referring to FIGS. 1, 2, and 3, the relief area is used to confine fluids added to the sample holder. The relief area is of a size that will not interfere with light incident on the disk from angles other than 90° or with the collection of light reflected from the surface of the disk when spectra are collected by reflectance.

Porous membrane 108 can be a separate membrane that is fixed in opening 106 or it can be integrally formed with body 102. Porous membrane 108 and disk 110 also may be formed as an integral structure.

In the preferred embodiment, the porous membrane 108 and disk 110 are an integrally formed structure and the disk/porous membrane are integrally formed with body 102. To facilitate this, body 102 is made from the same material as disk/porous membrane 108. However, the thickness of the disk/porous membrane 110 is not predetermined. All that is necessary is that disk/porous membrane have a thickness that will allow it to carry out its function for collecting cells and connecting to the frit of a vacuum flask. Moreover, the thickness of porous membrane 108 that is required it that it be sufficient to keep disk 110 flat under both positive and negative pressure.

Figure 4:
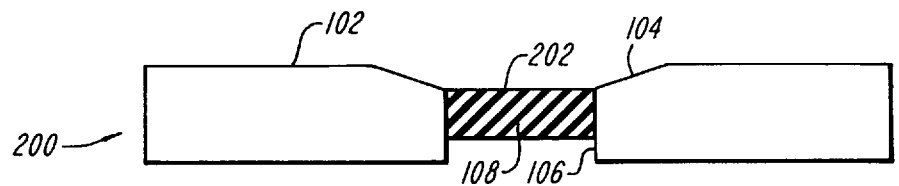
FIG. 4 is a cross-sectional view of a second embodiment of the sample holder of the present invention.

Referring to FIG. 4, a cross-sectional view of a second embodiment of sample holder of the present invention is shown. In this embodiment, the disk 202/porous membrane 108 structure shown generally at 200 does not have a metal coating as is shown for the sample hold structure in FIG. 1. Even though, the disk does not have metal coating, reflectance spectroscopy can still be used. Except for this difference in the disk, the second embodiment of the sample holder is substantially the same as the first embodiment.

Figure 5:
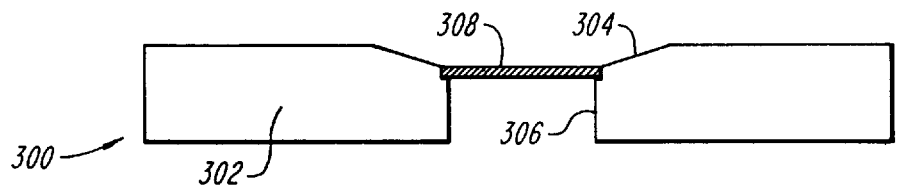
FIG. 5 is a cross-sectional view of a third embodiment of the sample holder of the present invention.

Referring to FIG. 5, a third embodiment of the sample holder of the present invention is shown generally at 300. The sample holder at 300 has body 302 and relief 304. Opening 306 is disposed through relief area 304. Disk 308 is disposed across opening 306. As is seen, this embodiment does not include a porous membrane to support the disk. For this embodiment to be used, there must be support provided by the frit of vacuum flask.

Referring to FIG. 6, a vacuum filtration system is shown generally at 400. Vacuum filtration system 400 is used for loading cells in suspension onto disk 308. The vacuum filtration system includes vacuum flask 406 and frit 405, which is disposed in opening 412 at the top of vacuum flask 406.

Vacuum flask 406 has vacuum outlet 408, which is connected to a vacuum pump (not shown) that will draw a predetermined level of vacuum in vacuum flask 406. Vacuum flask 406 also has drain outlet 410 to which a drain line (not shown) connects. Valve 411 is disposed in drain outlet 410 to control fluid drainage from vacuum flask 406.

Frit 405 has an outside contour and shape that permits it to sealingly fit in top opening 412 of vacuum flask 406. Frit 405 has top surface 403 and opening 407 in the bottom. Hollow nipple 404 extends upward from top surface 403. Hollow nipple 404 is in fluid communication with opening 407. Frit 405, preferably, is made from sintered glass or plastic.

Vacuum filtration system 400 is shown with a sample holder spaced slightly above it. As is shown, hollow nipple 404 is dimensioned to fit behind the porous membrane.

Although frit 405 is shown with hollow nipple 404 extending from up surface 403, the present invention contemplates other configurations of frit 405, which includes without limitation a flat frit with an opening to accommodate the size of porous membrane 308 and porous membrane 308 is disposed flush with the bottom of body 102. Moreover, the end of hollow nipple 404 may have a porous closure membrane that will support an unsupported disk as shown in FIG. 3.

Constructing frit 402 to the exact contour of body 102 and opening 106 of the sample holder insures efficient application of suction pressure through disk 110. As such, negative pressure that is applied through vacuum flask 406 does not rupture the disk or tear it from body 102. Therefore, all that happens when the vacuum is applied through causing suction through vacuum outlet 408 is disk 308 of the sample holder is drawn tightly to the surface of the sintered glass frit 405.

If the disk is not an integral part of the body, the body can be made from molded plastic or even non-wettable cardboard which will help hold the disk to the body. The body may be made from plastic and contains sintered, porous material, which provides the disk with a rigid backing. The requirements of the pore size in the porous membrane on which the disk is placed are that they do not impede suction of material onto and through the disk, and that they not be large enough to destabilize the rigidity of the backing of the disk because the disk must remain flat when subjected to negative or positive pressure. Pore size in the porous material will depend on the wettability of the material from which the body is constructed. Pore size of the porous material may be varied selectively by the operator to filter small to large cells.

In another preferred embodiment of the present invention, the sample holder body is transparent to visible light except for the disk/porous membrane disposed in the opening. This type of structure permits the user simultaneously to prepare cells on a sample holder for examination using vibrational spectroscopy and then for examination using standard microscopy. If cells are not to be examined by the second method (standard cytological methods), the requirement for the body to be transparent is unimportant.

A brush or other collecting device with cells scraped from an organ or tissue attached is scraped across the top of disk 308 of the sample holder while suction is applied from below. The collecting device, with attached cells, is moved back and forth across the disk and rotated simultaneously to effect transfer of cells from the collecting device to the disk, the vacuum will remove cells from the collecting devices and trap them on disk 308.

Once the cells are deposited on disk 308, they can be treated with fixative as set forth in copending application Ser. No. 08/485,366, titled "Biological Cell Sample Holding For Use In Infrared and/or Raman Spectroscopy Analysis" filed Jun. 7, 1995, Ser. No. 08/523,972, titled "A System and Method for Diagnosis of Disease By Infrared Analysis of Human Tissues and Cells," filed Jun. 7, 1995, or other chemicals for the purpose of enhancing the information to be collected from the cells by infrared spectroscopy. Any chemicals added to the cells, including fixative, can be given a predetermined reaction time and then removed by application of suction followed by washing the cells by filtration. The selection of sample holders with different pore sizes allows the operator to selectively retain cells of only specific sizes on the disk.

The sample holder of the present invention also can be used to separate cells from each other on a basis other than size. Disk 308 may be coated with reagents that react specifically with selected molecules on the surface of cells. For example, antibodies to react with CD4 determinants on the surface of T-lymphocytes. The passage of hetergenous mixtures of lymphocytes, whole blood, or other heterogeneous mixtures of cells through disks with pores larger than the diameters of lymphocytes will cause selective retention of CD4 positive T-lymphocytes on the disks. This selected population of T-lymphocytes then can be analyzed spectrally. This use of the disks for the selective concentration (with or without subsequent fixation) and then spectral analysis of defined populations of cells in heterogeneous mixtures of cells is generally and limited only by the kinds of reagents that can be prepared to select markers on the surfaces of different types of cells.

Figure 7:
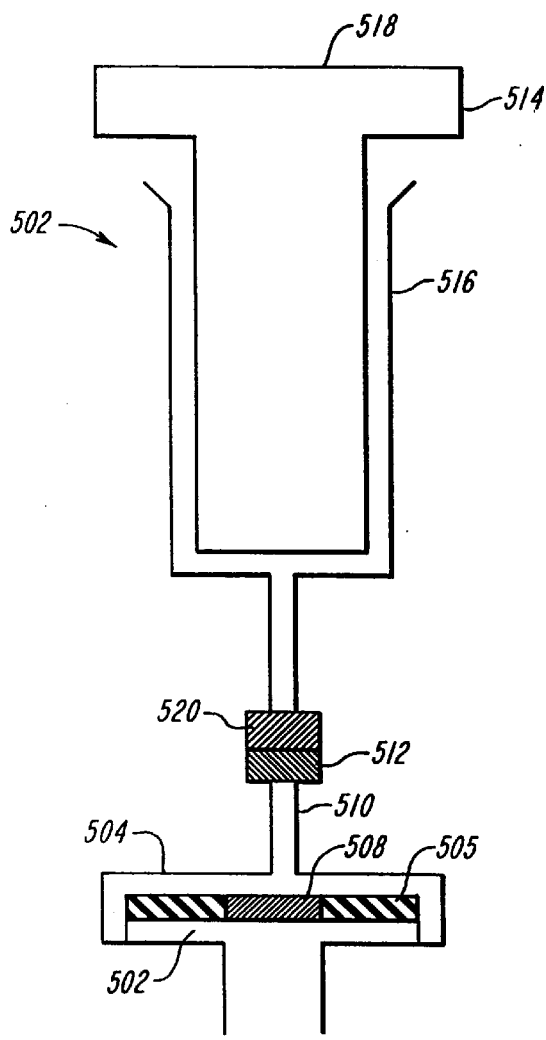
FIG. 7 shows an embodiment of a system of the present invention for collecting and concentrating cells.

Referring to FIG. 7, an alternative structure is disclosed for collecting and concentrating cells on the disk of a sample holder. In this structure, the cells are collected by collecting devices, such as brushes and spatulas, and added to a fluid. Then, the cells are filtered from the suspension through the disk of the sample holder. This method for preparing samples of cells for infrared spectroscopy may be used when the cells are in urine or other fluid. Cells added to the disk in this way may be fixed or treated with other chemicals prior to concentration on the disk, or they can be treated with fixatives and any other chemicals after concentration on the disk.

FIG. 7 at 500 shows another embodiment of the system for adding and concentrating cells on disk 508 for vibrational spectroscopic analysis, such as reflective infrared, Raman, and resonance Raman spectroscopy. Disk 508 is not attached permanently to frit 502 of filter holder 504 but is free. Disk 508 is disposed within filter holder 504 and filter holder 504 can be opened after use to remove disk 508. Filter holder 504 may be made of any suitable material.

Preferably, filter holder 504 includes frit 502 and cap 510. The frit and cap are made preferably from molded plastic. Cap 510 has a hollow membrane that extends upward from the top. Cap 510 and frit 502 sealably and detachability mate. Filter holder 504 holds disk 508 in place and prevents it from tearing when positive pressure is applied.

Figure 8:
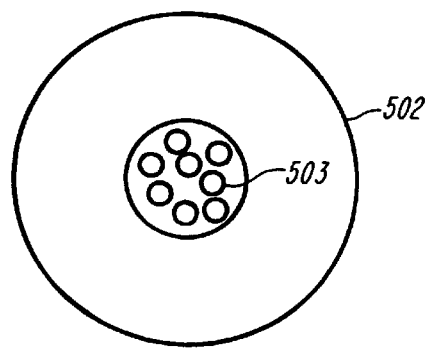
FIG. 8 shows a top view of a frit for use with the system shown in FIG. 7.

FIG. 8 shows a top view of frit 502. Frit 502 is disposed below disk 508 and has a plurality of openings 503 in fluid communication with flask 406.

Figure 9:
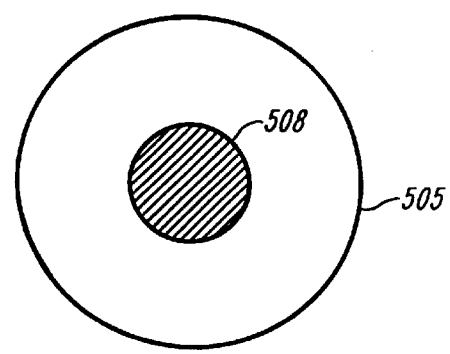
FIG. 9 shows a top view of the disk and non-porous transport support.

Referring to FIG. 9, disk 508 is bordered by a non-porous frame 505 that is disposed on frit 502. Frame 505 restricts the cells collected on disk 508 to a small area and facilitates manipulation of disk 508 after it is loaded with cells. syringe 514 The membrane that extends upward from the top of cap 510 connects to syringe 514 via Luer lock 512 or any other suitable attachment mechanism. Plunger 518 is disposed in the top end of syringe 514 for forcing fluid with cells down to disk 508. More specifically, the cells suspended in fluid medium with the barrel 516 of the syringe 514 are collected on disk 508 by applying positive pressure to plunger 510 and filtering the suspension through disk 508 that is held in filter holder 504. Once this is accomplished, disk 508 with attached cells is removed from filter holder 504 by grasping disk 508 via nonporous border 505. Filter holder 504 is discarded if it is made of plastic or other inexpensive materials or it can be washed for reuse if it is made of stainless steel or other expensive material. Disk 508 with trapped cells is removed and is mounted on an appropriate structure so the spectral analysis of the cells can be obtained.

The combination of vacuuming cells onto a porous grid followed by fixation provides a method that delivers cells to the cytology lab in a form requiring no further preparation for examination by vibrational spectroscopy. The sample holders with attached, fixed cells are ready for immediate spectral examination on reaching the laboratory. As such, the present invention permits immediate spectral analysis of the prepared cells at the site of their preparation.

The combination of the above methods for adding cells rapidly to disks and fixing them rapidly with high concentrations of fixative provides a method for archival transport and/or storage of cells. For example, cells prepared in the manner described above contain no potentially infectious or hazardous materials and can be mailed in a plain envelope. Since the cells on the disk are already stably fixed, they can be washed off the disk for subsequent examination by other methods for obtaining medically relevant information from cells.

The method just described has general application to the preparation of cells for spectral examination at the point of collection for any type of cell, as for example cervical cells removed by collecting brushes or spatulas, cells collected in urine, cells aspirated from any body cavity, and cells aspirated by thin needle biopsy techniques to name a few.

A still further embodiment of the present invention, will be described referring to FIG. 10.

Figure 10:
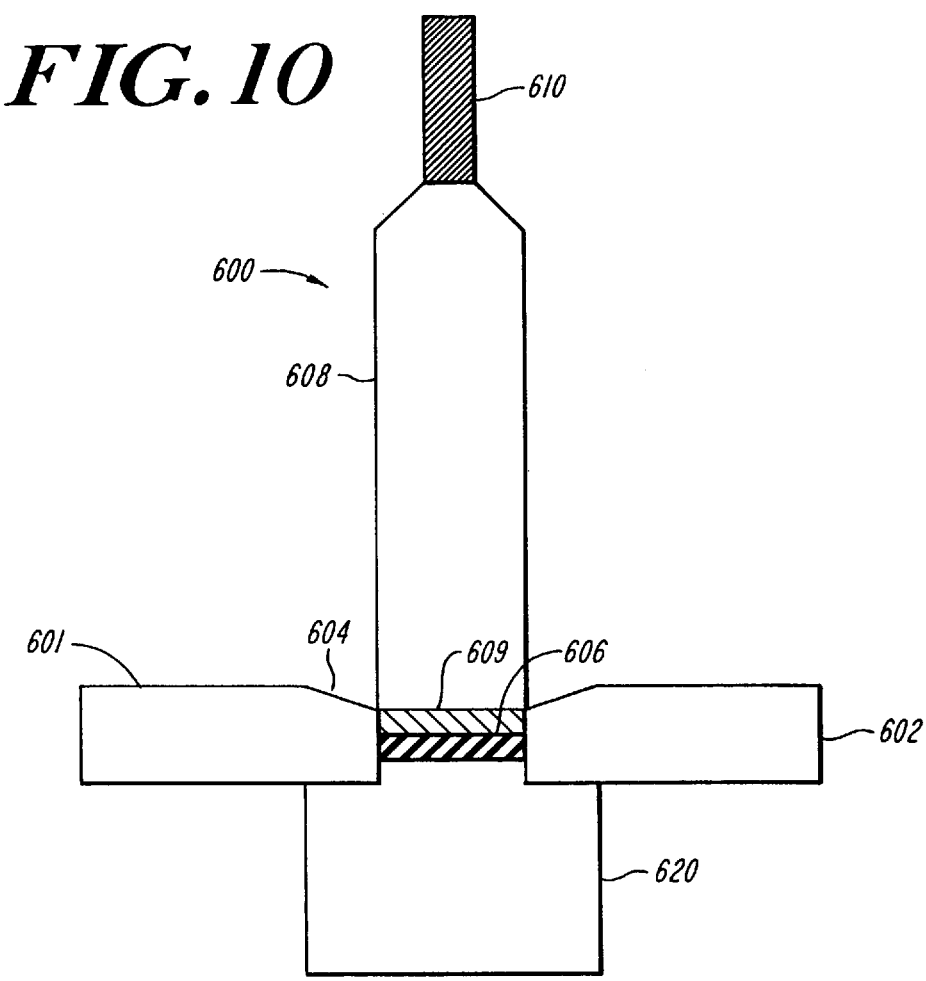
FIG. 10 shows another embodiment of a system of the present invention for collecting and concentrating cells.

Referring to FIG. 10, generally at 600, cells to be analyzed are collected directly with vacuum pipette 605. The vacuum pipette including hollow tube 608 with end membrane 610 having a porous collecting grid. The cells vacuumed from the surface of an organ, for example, the cervix, are deposited directly onto the porous collecting grid at 610.

The vacuum pipette includes hollow tube 608 with end membrane 610. This collecting grid is for coarse grating to remove cells and may be made of nylon, polyester, and other material with pores far larger than the sizes of epithelial cells being collected. The coarse, porous nature of the collecting grid allows cells to be scraped off and then to be pulled through the open end of the hollow tube by suction when the open end of tube 608 is disposed over disk 609 and porous membrane 606. Cells collected at the collecting grid may be washed through the tube, after removal of the tube from the organ of interest, by immersion in a suitable fluid while continuously applying vacuum to remove cells from hollow tube 608 and entrap them on disk 609 of the sample holder. Once this is done, hollow tube 608 is detached from the sample holder and cells are treated and analyzed spectrally.

Figure 11:
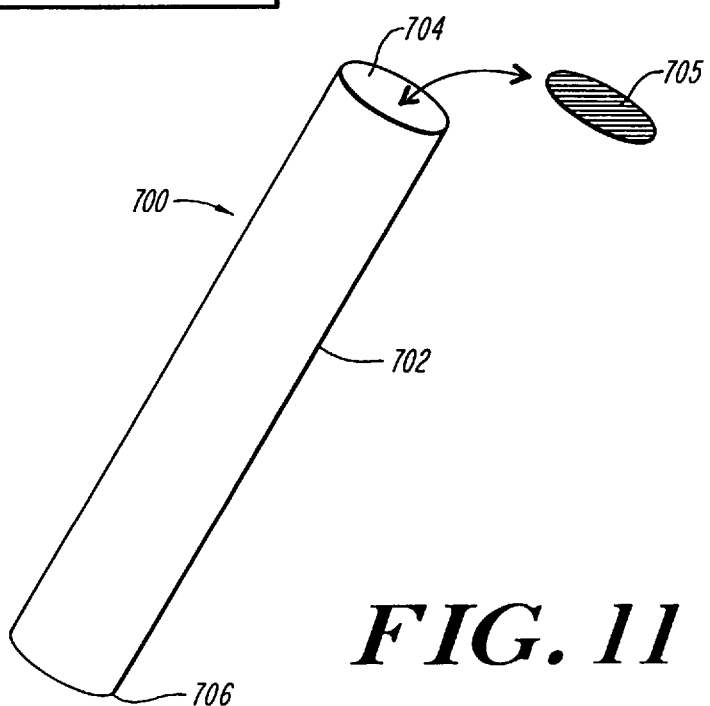
FIG. 11 shows an element for a collective system for use with a sample holder of the present invention.

A second embodiment of the collecting tube is shown generally in FIG. 11 at 700. According to this embodiment, hollow tube 702 has end 704 to which disk 705 may be attached. Open end 706 of tube 702 is for attachment to a vacuum line. To collect cells, end 704 with disk 705 disposed thereon is disposed in the organ of interest. After the cells are collected, the disk is removed and added to a sample holder for treatment of the cells.

Fixative is used to prepare cells for standard cytologic examination. After fixation, the cells are stained and then microscopic examination is carried out. Ethanol used in cytology cannot be used for fixing cells that will be examined at a later date by methods of vibrational spectroscopy. This fixation does not adequately preserve the infrared spectral details of fresh cells. However, a fixative known to be satisfactory for the fixation of cells for examination by vibrational spectroscopy, e.g., formaldehyde, may not be suitable for fixing cells for cytologic examination. This is so because the appearance of stained cells under the microscope depends on the nature of the fixative used to prepare them and because the features of cells identified in cytologic examinations as reflecting the presence or absence of disease are more familiar to cytologists when cells are fixed with ethanol as compared with formaldehyde. This alone makes it impossible to examine a single population of cells by both methods. Furthermore, staining of cells with the vital dyes used in histopathology and cytology introduces bands into vibrational spectra that overlap the bands due to the endogenous molecules of cells, which are the basis for making diagnoses on the basis of vibrational spectra. Finally, materials that are both transparent to visible light and inexpensive, e.g. glass, are not transparent to infrared light in all frequencies and especially in the mid infrared region (400–4000 $cm^{-1}$).

Referring to FIG. 1, the method of the present invention for preparing a single sample holder for vibrational spectroscopic and microscopic examination will be described. The sample holder is transparent to visible light everywhere except where the porous membrane and disk are located. However, these areas may be transparent to visible light. The disk/porous membrane of the sample holder have the properties, already described above, that make it suitable for adding cells and for obtaining vibrational spectra. Cells attached to a collection device, as described above, are scraped across the entire face of the sample holder, excluding the disk/porous membrane. This method transfers between 5–10 percent of the cells on the collecting device to the sample holder and is the standard cytological method for transferring cells from collecting devices to slides. The cells are then fixed, stained, and examined microscopically for evidence of disease. The transfer of cells from collecting devices to the non-disk area of the sample holder, in this way, requires a few seconds.

Once cells are deposited on the non-disk area of the sample holder, 90 percent of original cells remaining on the collecting device may be transferred to the disk of the sample holder by vacuum suction applied to the disk/porous membrane. The cells on the disk of the sample holder are then fixed by draining a suitable fixative through the disk/porous membrane followed by washing the cells free of fixative.

The cells on the non-disk area of the sample holder are then fixed by spraying with alcohol mixtures in the usual way for preparing slides for cytology. The spectral analysis of the cells must be taken prior to staining of the cells.

This embodiment also can be used to prepare cells on a single sample holder for spectroscopic and cytologic examination from fine needle aspirates of solid tissues or bone marrow. Cells of interest are aspirated into a syringe and then deposited, by applying positive pressure to the plunger of a syringe, on the appropriate regions of the sample holder.

Reflectance spectroscopy of cells can be used to obtain spectral data using the present invention. This is done by transferring cells from collecting devices to sample holders by scraping the brush across a suitably coated, non-porous surface of the sample holder. The sample holder body consists of solid, non-infrared transparent material which is coated with metal or contains a small "disk-like" area that is metal coated. Cells are deposited on the small metal coated region of the sample holder by scraping a collecting device, a brush or spatula, across the surface of the sample holder in the same way that cells are transferred to sample holders for standard cytological examination. Cells deposited on the metal-coated area of the sample holder are then studied using reflectance spectroscopy. This method is less suitable than filtration of cells onto disks because fewer cells are collected by scraping than by filtering or vacuuming cells onto disks. But the method of scraping is well-suited for examination of cells on a one by one basis using reflectance spectroscopy via microscopic optics.

The terms and expressions which are used herein are used as terms of expression and not of limitation. There is no intention in the use of such terms and expressions of excluding the equivalents of the features shown and described, or portions thereof, it being recognized that various modifications are possible in the scope of the present invention.

We claim:

1. A sample holder for collecting and concentrating cells for use in vibrational spectroscopy, comprising:

a central body having a predetermined shape;

a relief area disposed in the central body;

an opening disposed in through the central body at the relief area; and a porous structure disposed in the opening with the porous structure including pores of predetermined size for filtering cells of a predetermined size.

2. The sample holder as recited in claim 1, wherein the porous structure further comprises a porous membrane with a porous disk disposed at one surface.

3. The sample holder as recited in claim 2, wherein the disk is metal coated.

4. The sample holder as recited in claim 2, wherein the porous membrane supports the disk.

5. The sample holder as recited in claim 1, wherein the porous structure further comprises a disk.

6. The sample holder as recited in claim 5, wherein the disk is metal coated.

7. A sample holder for collecting and concentrating cells for use in reflectance spectroscopy, comprising:

a central body having a predetermined shape;

a relief area disposed in the central body;

an opening disposed in through the central body at the relief area; and a porous structure comprising a metal-coated disk disposed in the opening with the porous structure including pores of predetermined size for filtering cells of a predetermined size.

8. A system for collecting and concentrating cells comprising:

a central body having a predetermined shape;

a relief area disposed in the central body;

an opening disposed in through the central body at the relief area;

a porous structure comprising a metal-coated disk disposed in the opening with the porous structure including pores of predetermined size for filtering cells of a predetermined size; and a tube membrane with a first open end for disposition over the disk, the tube membrane further including an elongated membrane with a reduced diameter at a second end, with the reduced diameter being porous with a predetermined pore size.

* * * * *